(12) United States Patent
Lohr et al.

(10) Patent No.: US 6,508,132 B1
(45) Date of Patent: Jan. 21, 2003

(54) DYNAMIC LOAD CELL APPARATUS

(75) Inventors: Raymond David Lohr, Long Crendon (GB); Paul Derek Hayford, Holmer Green (GB); Chanchal Singh Bahra, Workingham (GB)

(73) Assignee: Instron Corporation, Canton, MA (US)

( * ) Notice: Subject to any disclaimer, the term of this patent is extended or adjusted under 35 U.S.C. 154(b) by 0 days.

(21) Appl. No.: 09/251,533

(22) Filed: Feb. 17, 1999

(51) Int. Cl.$^7$ .................................................. G01L 1/00
(52) U.S. Cl. ............................. 73/760; 73/767; 73/73; 73/769
(58) Field of Search .......................... 73/862, 381, 722, 73/781, 767, 769, 760; 340/680

(56) References Cited

U.S. PATENT DOCUMENTS

| | | | | |
|---|---|---|---|---|
| 4,047,144 A | * | 9/1977 | Wong | 338/2 |
| 4,478,086 A | * | 10/1984 | Gram | 73/781 |
| 5,739,411 A | * | 4/1998 | Lee et al. | 73/12.13 |
| 5,798,462 A | * | 8/1998 | Briefer et al. | 73/722 |
| 6,114,965 A | * | 9/2000 | Schoch | 340/680 |

* cited by examiner

Primary Examiner—Benjamin R. Fuller
Assistant Examiner—Andre Allen
(74) Attorney, Agent, or Firm—Gary R. Jarosik; Mark R. Gals

(57) ABSTRACT

A load cell for use in dynamic testing apparatus for mechanically testing samples includes an accelerometer mounted in the load cell on the same axis as the line of action of the mechanical force applied to the specimen under test. The resultant signal from the combination of the normal output from the load cell and the output from the accelerometer compensates for errors introduced by the mass of the moving grip used to grip the specimen in the apparatus.

5 Claims, 3 Drawing Sheets

DYNAMIC LOAD CELL APPARATUS

BACKGROUND OF THE INVENTION

The present invention relates to apparatus for the dynamic testing of materials and structures and more particularly to a load cell for use in such apparatus.

Such apparatus is well known and FIG. 1 shows a typical arrangement where a specimen 10 to be tested is mounted in a framework 11 by means of two grips 12 and 13. One of the grips, in this case the grip 13, is connected to a suitable load applying device such as an hydraulic actuator for moving the grip while the other grip, in this case the grip 12, is connected to a load cell for monitoring the forces placed on the specimen by the load applying device. When testing dynamically, utilising frequencies over say 10 Hz, the force indicated by the load cell 15 equals the force in the specimen 10 and the inertia force generated by the grip between it and the load cell, in this case the grip 12. In other words, this can be expressed as:

$F_{cell} = F_{specimen} + ma$

Where $F_{cell}$ is the force seen at the load cell, $F_{specimen}$ is the force seen at the specimen, "m" is the mass of the grip or fixture between the specimen and the cell and "a" is the acceleration of the grip or fixture. The inertia force "ma" is of course an unwanted error signal and needs to be removed in order to measure specimen forces accurately.

Historically, the error caused by the inertia force has either been unappreciated or else ignored. However, the error magnitude can easily amount to 10% of the actual force and considerably more if mechanical resonances in the system enhance the local grip acceleration. As a result, fatigue data accuracy is potentially compromised. This can have serious safety consequences when the parts undergoing fatigue testing in service are aircraft or automotive components such as critical fasteners.

Further on uncompensated systems, inertia force errors at high frequencies, circa 100 Hz, can cause load control loops to become prematurely unstable, particularly when testing compliant specimens.

Previously it has been proposed to try and correct the inertia force error by using a separate accelerometer fixed to the grip between the specimen and the cell in order to provide a proportional signal which is used to correct the load cell output signal. While this system was an improvement on the original uncompensated system, it still did not totally correct for the inertia force error.

SUMMARY OF THE PRESENT INVENTION

It is an object of the invention to provide accurate correction of the error caused by the grip inertia in an apparatus for dynamically testing objects.

In the present invention, this is achieved by placing an accelerometer within the load cell on the same axis as the force applied to the object under test.

Preferably, the signal from the accelerometer is fed with a signal derived from the load cell down a single cable and then combined with the load cell signal at the testing machine structural rig controller and digitised.

In addition to providing an accurate result, dynamic calibration of the apparatus can be automated enabling rapid optimisation of the apparatus to a new set-up where the grip mass may have changed. Also, the frequency range over which valid testing can be carried out is increased, enabling fatigue tests to be completed much more quickly. As an example, the time to apply ten million cycles (typical for high cycle fatigue testing) at 20 Hz is about 6 days non-stop whereas at 60 Hz it reduces to 2 days. This offers major cost savings to users of existing fatigue testing machines by upgrading their load cells and controller.

Furthermore, inertia compensation enables a much tighter load control loop giving greater bandwidth and more accurate control.

Finally, the invention provides good force measurement and control when the load cell is mounted to the moving end of the actuator piston, where accelerations are significant, such as in many bio-mechanics and structural rig applications.

BRIEF DESCRIPTION OF THE DRAWINGS

In order that the present invention be more readily understood, the preferred embodiment will now be described with reference to the accompanying drawings in which.

DESCRIPTION OF THE PREFERRED EMBODIMENT

Figure 1:
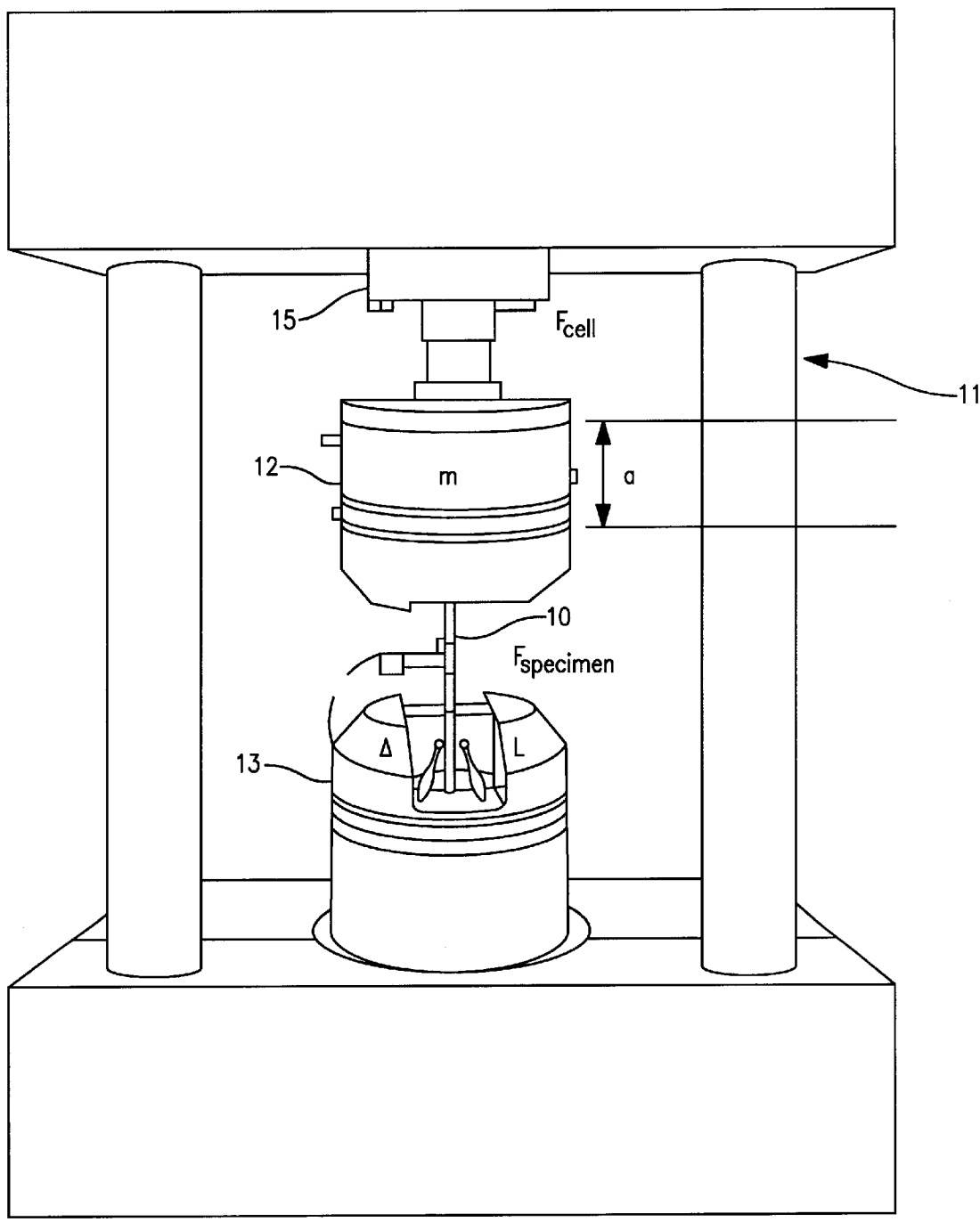
FIG. 1 shows a diagram of a basic form of testing apparatus.
Figure 2:
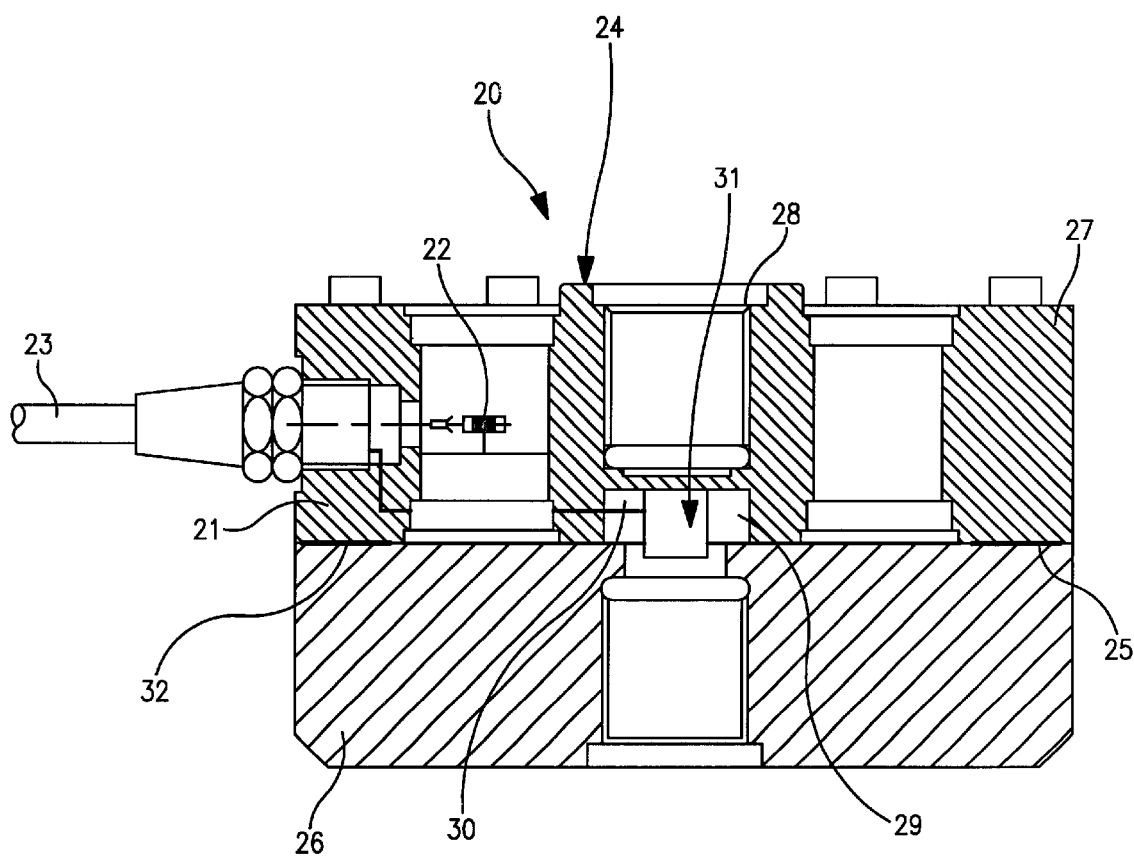
FIG. 2 shows a cross sectional view through a load cell according to the present invention for use with the apparatus shown in FIG. 1.

The present invention is a load cell arranged to be used in the apparatus shown in FIG. 1 in order to greatly improve the accuracy of measurement of the apparatus under dynamic testing conditions. Referring to FIG. 2, the load cell which is indicated generally by the reference numeral 20 will be seen to comprise a generally cylindrical housing 21 arranged to receive one or more (in this case 8) force measuring devices in the form of electromechanical transducers 22. In the present embodiment the force measuring devices are strain gauges, only one being shown in FIG. 2, symmetrically mounted on radial webs connecting the central hub to the outer flange of the body 21.

The outputs from the force measuring devices 22 are electrical signals which are fed down a cable 23 to control and measuring apparatus which is not shown in the present application due to the fact that it is largely well known in the art.

One end of the body 21, in this case the end 25, is provided with a flange 26 by means of which the load cell is fixedly mounted in the testing apparatus by means of a central fixing. The other end 27 of the body is arranged to be provided with a central fixing hole 28 by means of which the load cell can be attached to the grip 12 shown in FIG. 1.

It will be seen from FIG. 2 that the fixing hole 28 is a screwed recess which does not extend the full depth of the body 21. Aligned with the fixing means 28 but extending from the end 25 of the body is a further recess 29, the bottom of which forms a mounting surface 30. Attached to the mounting surface 30 on the centre line of the fixing hole 28 is an accelerometer 31. Depending on the exact size and shape of the accelerometer and body, it may be necessary to provide an aperture in the meeting surface of the flange 26 in order to ensure correct operation of the accelerometer.

The output of the accelerometer is an electrical signal which is fed via a conductor 32 so as to be fitted into the cable 23.

With this construction, the accelerometer is at the heart of the load cell, directly on the load string axis. The arrangement and depths of hole 28 and recess 29 are such that the accelerometer senses the load acceleration of the hub of the load cell nearer to the test object. This removes the risk of errors in the acceleration reading resulting from off-center loading. In comparison with the previous attempt to provide a solution to the problem, this has the following advantages:

(a) The accelerometer is on the load line eliminating "Abbe" measurement errors;

(b) The accelerometer is rigidly connected to the adjacent grip eliminating amplitude and phase errors;

(c) Automatic set-up takes less than one minute; and (d) Set-up is consistent and reliable between operators.

The conditioning of the acceleration signal is handled as standard and is set-up automatically when the system is auto tuned. This means that time is saved and operator errors reduced. For users who wish to do this themselves they have the option to switch this feature on or off and set the correction factor manually. The resulting signal is then subtracted from the load cell signal. That is:

$F_{cell} = F_{specimen} + ma - ka_c$

Where k is the correction factor and $a_c$ is the signal from the accelerometer 31. The result is that $F_{cell} = F_{specimen}$.

Figure 3:
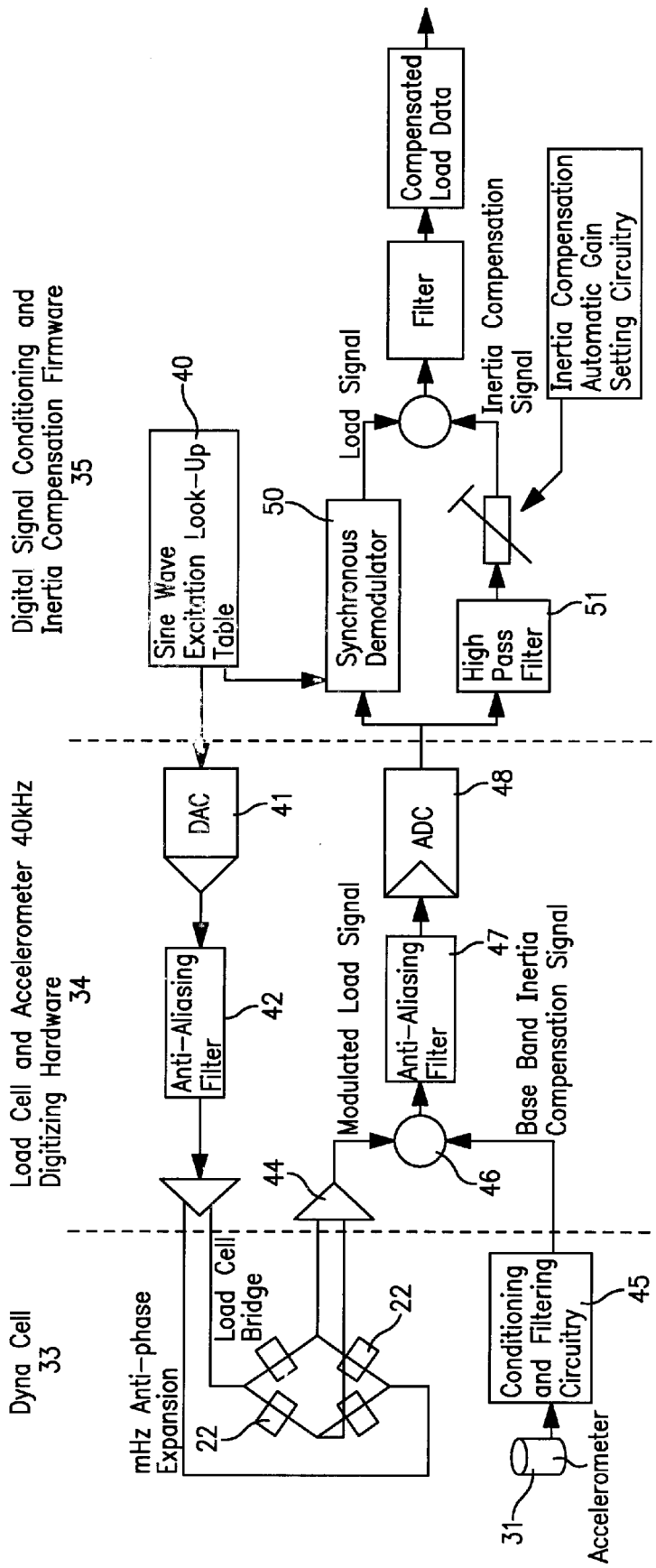
FIG. 3 shows a circuit diagram showing the electronic circuitry for processing these signals produced from the load cell shown in FIG. 2.

For completeness, a block diagram of the electronic circuitry for producing a compensated signal is shown in FIG. 3. The circuitry consists of three basic components namely the circuitry 33 associated with the load cell, digitising circuitry associated with the circuitry 33 and digital signal conditioning and inertia compensation embedded software 35 associated with the digitising circuitry 34.

In order to conduct a dynamic test, a drive signal is derived from a sine wave excitation look up table 40 and supplied to the force measuring transducers 22 in the load cell via a digital analogue converter 41 and an anti-aliasing filter 42. The force measuring transducers 22 are arranged in a bridge configuration and produce a modulated load signal output via a differential amplifier 44.

The output from the accelerometer 31 is fed through conditioning and filtering circuitry 45 in order to produce a base band inertia compensation signal which is added to the modulated load signal at a summing function 46 and then via an anti-aliasing filter and analogue to digital converter 48 back to the digital signal conditioning and inertia compensation embedded software 35.

The output from the analogue to digital converter 48 is fed to a synchronous demodulator 50 where it is processed with the output from the sign wave excitation look up table 40 in order to produce a load signal output. The output from the analogue to digital converter 46 is also fed to a high pass filter 51 and from there to inertia compensation automatic gain setting circuitry in order to provide the inertia compensation signal which is added to the load signal and a compensated load data signal is thus produced.

This circuitry allows automatic set-up and therefore reduces operator errors and improves system integrity.

The apparatus, as a whole, reduces dynamic load errors which can be a significant percentage of reading and increases productivity by allowing higher frequency operation while maintaining test validity. Doubling of the frequency of operation is readily achievable.

While the above description has been given in relation to an arrangement whereas the grip is connected to the load cell and the other grip is connected to the load applying device, it is possible to attach the load applying device to the load cell and then to the upper grip. Other variations and modifications will be apparent to these skilled in the art without departing from the spirit and scope of the invention which is set out in the following claims.

What is claimed is:

1. A load cell for use in an apparatus which tests an object by applying a dynamic force to the object, the load cell comprising:

a housing to which the object is connected;

a plurality of strain-gauges mounted in the housing for measuring a sensed force in response to the dynamic force being applied to the object;

an acceleration sensor mounted in the housing for measuring a local acceleration of the housing nearest to the object in response to the dynamic force being applied to the object; and circuitry associated with said acceleration sensor by which the local acceleration measured by the acceleration sensor is used to correct the sensed force measured by the plurality of strain-gauges to thereby provide a more accurate measurement of the dynamic force applied to the object.

2. The load cell as recited in claim 1, wherein the dynamic force is applied to the object along a line of action and the acceleration sensor is mounted in the housing on the line of action.

3. The load as recited in claim 2, wherein the acceleration sensor is an accelerometer.

4. An apparatus for testing an object, comprising:

a frame;

first and second grips mounted in the frame for gripping the object;

a means associated with the frame for applying a dynamic force to the first grip to thereby apply a force to the object;

a load cell connected to the second grip and to the frame, wherein the load cell comprises a housing, a plurality of strain gauges mounted in the housing for measuring a sensed force in response to the force being applied to the object, and an acceleration sensor mounted in the housing for measuring a local acceleration nearest to the object in response to the dynamic force being applied to the object; and circuitry associated with said acceleration sensor by which the local acceleration measured by the acceleration sensor is used to correct the sensed force measured by the plurality of strain-gauges to thereby provide a more accurate measurement of the dynamic force applied to the object.

5. The apparatus as recited in claim 4, wherein the two grips, the object under test, the load cell, and the acceleration sensor are axially aligned.

* * * * *